US 6,607,528 B1

(12) United States Patent
Quick et al.

(10) Patent No.: US 6,607,528 B1
(45) Date of Patent: Aug. 19, 2003

(54) SHAPEABLE ELECTROSURGICAL SCALPEL (75) Inventors: Richard L. Quick, Mission Viejo, CA (US); Martin Shabaz, Lake Forest, CA (US); Dan Kussman, Aliso Viejo, CA (US); Paul Lubock, Laguna Niguel, CA (US)

(73) Assignee: SenoRx, Inc., Viejo ( * ) Notice: Subject to any disclaimer, the term of this patent is extended or adjusted under 35 U.S.C. 154(b) by 0 days.

(21) Appl. No.: 09/752,265

(22) Filed: Dec. 29, 2000

Related U.S. Application Data (63) Continuation-in-part of application No. 09/337,666, filed on Jun. 22, 1999, now Pat. No. 6,267,759.

(51) Int. Cl.[7] .............................................. A61B 18/18
(52) U.S. Cl. ......................................... 606/45; 606/48
(58) Field of Search ........................... 606/41, 43, 45, 606/48, 50; 174/113 AS, 115

(56) References Cited

U.S. PATENT DOCUMENTS

| 3,884,237 | A | | 5/1975 | O'Malley et al. ............. 128/303 |
| 3,955,578 | A | | 5/1976 | Chamness et al. |
| 4,043,342 | A | | 8/1977 | Morrison, Jr. |
| 4,472,595 | A | * | 9/1984 | Fox et al. ...................... 174/36 |
| 4,823,791 | A | | 4/1989 | D'Amelio et al. |
| 4,832,048 | A | * | 5/1989 | Cohen ......................... 600/374 |
| 4,919,129 | A | * | 4/1990 | Weber et al. .................. 604/35 |
| 5,009,656 | A | | 4/1991 | Reimels |
| 5,041,124 | A | | 8/1991 | Kensey |
| 5,088,998 | A | | 2/1992 | Sakashita et al. .............. 606/46 |
| 5,089,002 | A | | 2/1992 | Kirwan, Jr. |
| 5,197,963 | A | * | 3/1993 | Parins .......................... 606/41 |
| 5,312,327 | A | * | 5/1994 | Bales et al. ................... 604/21 |
| 5,318,565 | A | * | 6/1994 | Kuriloff et al. .............. 604/119 |
| 5,417,687 | A | | 5/1995 | Nardella et al. ............... 606/32 |
| 5,437,665 | A | | 8/1995 | Munro ......................... 606/47 |
| 5,460,629 | A | | 10/1995 | Shlain et al. .................. 606/46 |
| 5,676,663 | A | | 10/1997 | Kim ............................. 606/45 |
| 5,735,847 | A | | 4/1998 | Gough et al. |
| 5,741,225 | A | * | 4/1998 | Lax et al. ..................... 604/22 |
| 5,810,806 | A | | 9/1998 | Ritchart et al. |
| 5,951,550 | A | | 9/1999 | Shirley et al. ................ 606/45 |
| 5,951,551 | A | * | 9/1999 | Erlich .......................... 600/45 |
| 6,036,681 | A | | 3/2000 | Hooven ....................... 604/506 |
| 6,102,907 | A | * | 8/2000 | Smethers et al. ............. 606/40 |
| 6,106,524 | A | * | 8/2000 | Eggers et al. ................. 606/41 |
| 6,231,591 | B1 | * | 5/2001 | Desai ............................ 604/8 |
| 6,251,121 | B1 | * | 6/2001 | Saadat ........................ 128/898 |
| 6,355,034 | B2 | * | 3/2002 | Cosmescu .................... 606/41 |

FOREIGN PATENT DOCUMENTS

| DE | 3804849 | 2/1988 |
| WO | WO 92/20291 | 11/1992 |
| WO | WO 94/17856 | 8/1994 |
| WO | WO 98/43531 | 10/1998 |
| WO | WO 99/37227 | 7/1999 |

OTHER PUBLICATIONS

International Search Report for PCT/US01/48233, mailed Oct. 14, 2002.

* cited by examiner

Primary Examiner—Roy D. Gibson
(74) Attorney, Agent, or Firm—Coudert Brothers LLP (57) ABSTRACT The invention is directed to an electrosurgical device having a shapeable elongate cutting electrode having a free distal end with an exposed length of at least about 0.25 inch and secured by its proximal end to the distal end of a handle. The electrosurgical device is designed for use with a high frequency electrosurgical generator which has an output at a frequence of between about 1 MHz and about 10 MHz, preferably about 3 to about 8 MHz. Preferably, the output has an essentially sinusoidal waveform with little harmonic distortion. The methods provide for the enhanced cutting of a variety of tissue including muscular, connective, glandular and fatty tissue. The device is particularly suitable in performing a breast biopsy.

73 Claims, 7 Drawing Sheets

SHAPEABLE ELECTROSURGICAL SCALPEL

RELATED APPLICATIONS

This application is a continuation in part of U.S. patent application Ser. No. 09/337,666, filed Jun. 22, 1999 now U.S. Pat. No. 6,267,759, by Richard Quick.

BACKGROUND OF THE INVENTION

Surgical lesion removal has traditionally been performed using a variety of surgical tools and techniques, some of which are specially adapted for a particular procedure. For example, large lesion removal from, e.g., the human breast, is typically attempted through an open incision using an ordinary surgical knife or scalpel. While the use of scalpels is widely accepted, they are not designed to minimize the invasiveness of a surgical procedure. During a surgical procedure, it is usually necessary to form an incision which is much larger than the lesion which is targeted for removal, so that the surgeon can work around, under, and over the lesion to remove both the entire lesion and a margin of tissue surrounding the lesion. The removal of a margin of tissue around the lesion is typically indicated, to be more certain that all of the lesion has been removed by the surgical procedure.

While the practice of removing tissue adjacent to a tissue mass of interest, e.g., a malignant or benign lesion, is followed in many lumpectomy procedures, the tools provided for a surgeon to remove the tissue are not well suited for performing the procedure. Straight and sculpted blade scalpels do not assist the surgeon in making the smallest cut necessary, and often require the surgeon to essentially dig out the tissue mass. The damage to the remaining tissues can be significant, resulting in considerable postoperative pain, excessive bleeding, long recovery times, the potential for infection, the potential for depression of the tissues at the surgical site (poor cosmesis) due to the removal of excessive tissue, and surface tissue scarring which is much larger than necessary. Furthermore, use of these conventional tools and techniques may cause excessive damage to the removed tissue and thus create a tissue specimen having ragged and irregular margins or borders. This, in turn can lead to inaccurate pathology studies of the excised tissue. There are some practitioners who believe that a significant number of negative pathology reports (i.e. reports which indicate that the specimen margins are clear of malignant tissue) are false negatives that will most likely result in recurrence of cancer in the patient. It is felt that a surgical device that results in smooth uniform margins would result in far more accurate pathology reports, particularly with patients who have or who are thought to have breast cancer. Patient management based on these more accurate reports would in turn lead to lower recurrence in breast cancer patients.

Breast cancer is presently the most common cancer in women and is the second leading cause of cancer deaths in women. With approximately one in eight American women developing breast cancer sometime in her lifetime, it is apparent that improved methods of diagnosis, such as breast biopsy are needed.

Electrosurgical devices have previously been used for tissue cutting, and surgical procedures. However, such devices typically use small, often pointed active cutting surfaces and the types of devices available to the surgeon who uses electrosurgery are limited. Furthermore, breast tissue and various other tissues are heterogeneous tissues and contain a variety of tissue types such as connective tissue, glandular tissue, vascular tissue, and adipose (fatty) tissue. Connective glandular and vascular tissues have similar characteristics in the way they react to high frequency electrical energy and hence the electrosurgical device. However, adipose (fatty)) tissue presents a higher impedance to the flow of electrical current than do the other types of tissues, and presents more difficulty in cutting. Thus, during an electrosurgical procedure if fatty tissue is encountered, a surgeon must perform surgical cuts by "feathering", making repetitive shallow cuts over the same area to attain a desired depth of cut. These repetitive shallow cuts expose the patient to an increased risk of receiving an unnecessary amount of electrical energy, greater injury to surrounding tissues, greater risk of infection, as well as potentially creating ragged or irregular margins in biopsied tissues.

From the discussion above, it should be apparent that there is need in the art for more effective surgical cutting devices which lead to less trauma to the surrounding and biopsied tissues and which can provide biopsy specimens having smooth regular margins. Furthermore there is a need in the art for additional types of tools used in electrosurgery which give the operator greater control over the types and configurations of cuts made in tissue during a surgical procedure. The present invention fulfills these needs.

SUMMARY OF THE INVENTION

The invention is directed generally toward an electrosurgical device for cutting tissue, and the method of use, which is particularly suitable for cutting heterogeneous tissue such as found in breast tissue.

The electrosurgical device embodying features of the invention has a handle and an elongated cutting electrode which is secured to the handle and which is configured to be electrically connected to a high frequency power source. The cutting electrode is an elongated conductive member with a free distal end and is preferably manually shapeable. The cutting electrode has an exposed cuffing length of at least 0.5 inch (1.3 cm), and may extend up to 4 inches (10.2 cm). Preferably, the cutting electrode can have an exposed length ranging from about 0.8 inch to about 2.8 inches (2–7 cm). In other embodiments, the cutting electrode can have an exposed length in the range of about 1.2 inches to about 2.5 inches (3–6.4 cm). The elongated cutting. electrode may be provided with an exterior insulating jacket which is slidable along the cutting electrode to allow the operator to adjust the length of the cutting electrode which is exposed.

The cutting electrode has a maximum transverse cross-sectional dimension of about 0.007 to about 0.03 inch (0.18–0.76 mm), preferably about 0.008 to about 0.02 inch (0.2–0.5 mm). Elongated cutting electrodes having transverse dimensions of this magnitude may cut large areas of tissue, particularly adipose tissue, with a very effective "clean sweeping motion" with very little pressure against the tissue, thereby creating less trauma to the surgical site and providing for smoother margins of excised tissues. For increased electrode flexibility, the distal section of the cutting electrode may be distally tapered to smaller transverse dimensions. For example, the distal section may taper from a transverse dimension of about 0.01 to about 0.02 inch (0.25–0.51 mm) at the proximal section of the electrode to a smaller transverse dimension of about 0.004 to about 0.01 inch (0.1–25.4 mm) at a distal end of the tapered distal length.

A cutting electrode embodying features of the invention is formed of a conductive material and is preferably formed of a high strength metallic material such as tungsten, and alloys thereof and particularly tungsten alloys containing about 3 to about 25% (wt %) rhenium. The tungsten containing cutting electrodes are very suitable with high frequency electrical power. In alternative embodiments which operate at lower frequencies (e.g. less than about 2 megahertz) the electrode may be made of stainless steel and other metallic compositions.

The electrosurgical devices are preferably part of an electrosurgical system which includes a high frequency (e.g. RF) electrosurgery generator that is electrically coupled to the electrosurgical device. The high frequency generator is preferably configured to produce electrical power in a frequency range of about 1 to about 10 megahertz, particularly a frequency range of about 3 to about 8 megahertz with a current output of up to 4 amps. The voltage capacity is about 150 Vrms to about 800 Vrms to facilitate a wide variety of procedures, including coagulation at the lower voltages (e.g. about 150 to about 300 Vrms) and heterogeneous tissue cutting at the higher voltages (e.g. about 400 to about 800 Vrms). When cutting through heterogeneous tissue the voltage is controlled to a first range of about 550 to about 650 Vrms, typically about 600 Vrms during the initiating of the cut and then controlled at a lower level between about 450 and about 550 Vrms, typically about 480–500 Vrms. Amperage also may vary between initiation, e.g. about 1.75 amps, and normal running, e.g. about 1 amp.

The duty factor and the voltage generally should be higher at the initiation of the cut and less during the running period. For example, the duty factor may range from about 2 to about 10% up to 100% at a frequency of about 10 Hz up to the output frequency; however, generally the duty factor frequency is above 30 kHz with 50 kHz being typical.

The high frequency output of the electrical power generator has a periodic output and preferably has an essentially sinusoidal waveform and most preferably with a total harmonic distortion of less than about 5%. To complete the electrical circuit at least one additional electrode is needed to be in contact with the patient for a monopolar electrical configuration or on the electrosurgical cutting device for a bipolar mode. In one version of the invention the system has an electrode pad which is secured to the patient's exterior close to the electrosurgical site to complete the electrical circuit.

The power cable directing high frequency electrical power from the electrical generator should be shielded cable and be flexible enough so that it does not interfere with the physician's (or other operator's) handling of the electrosurgical device during the procedure. One cable construction which has, been found to be very suitable has a central metallic conductor disposed within an outer jacket with a space between the central conductor and the inner surface of the jacket in order to reduce cable capacitance. The jacket has an outer polymer layer, an inner polymer layer and a shielding layer such as metallic braid, spiral wrap or foil disposed between the inner and outer layers. The inner polymer layer is essentially non-conductive. The central conductor is not supported within the jacket, it is essentially free floating, so it will contact the inner surface of the jacket at multiple locations when the cable is bent during use. However, the capacitance of the cable remains relatively constant because the off-center conductor averages to be the same as an on center conductor.

The invention may also be directed toward a method of performing tissue excision wherein an electrosurgical device is provided having a shapeable elongated electrode with a proximal end that is electrically connected to a high frequency power source and a distal end have a length of exposed cutting surface. The device preferably has a handle configured to hold the electrode and preferably have a mechanism to extend a desired length of exposed electrode out the distal end of the handle for a particular use. The elongated cutting electrode may be preshaped to a desired configuration in its manufacturing process or it may be manually shaped by the physician or other operator just prior to or during the procedure. The cutting electrode is placed in contact with the tissue to be excised and the electrosurgical device is then energized by providing RF power to the cutting electrode from a high frequency power generator. The cutting electrode will readily and smoothly pass through a variety of tissue types including muscular, connective, glandular and fatty tissue. The electrosurgical device may also be energized by the high frequency power generator with wave forms suitable for coagulation of bleeding vessels and tissue. A finger actuated switch on the handle or a dual foot switch situated on the floor allow the user to choose the cutting or the coagulation modes. Other modes may also be provided for other procedures.

These and other advantages of the invention will become more apparent from the following detailed description thereof and accompanying exemplary drawings.

DETAILED DESCRIPTION OF THE INVENTION

Figure 1:
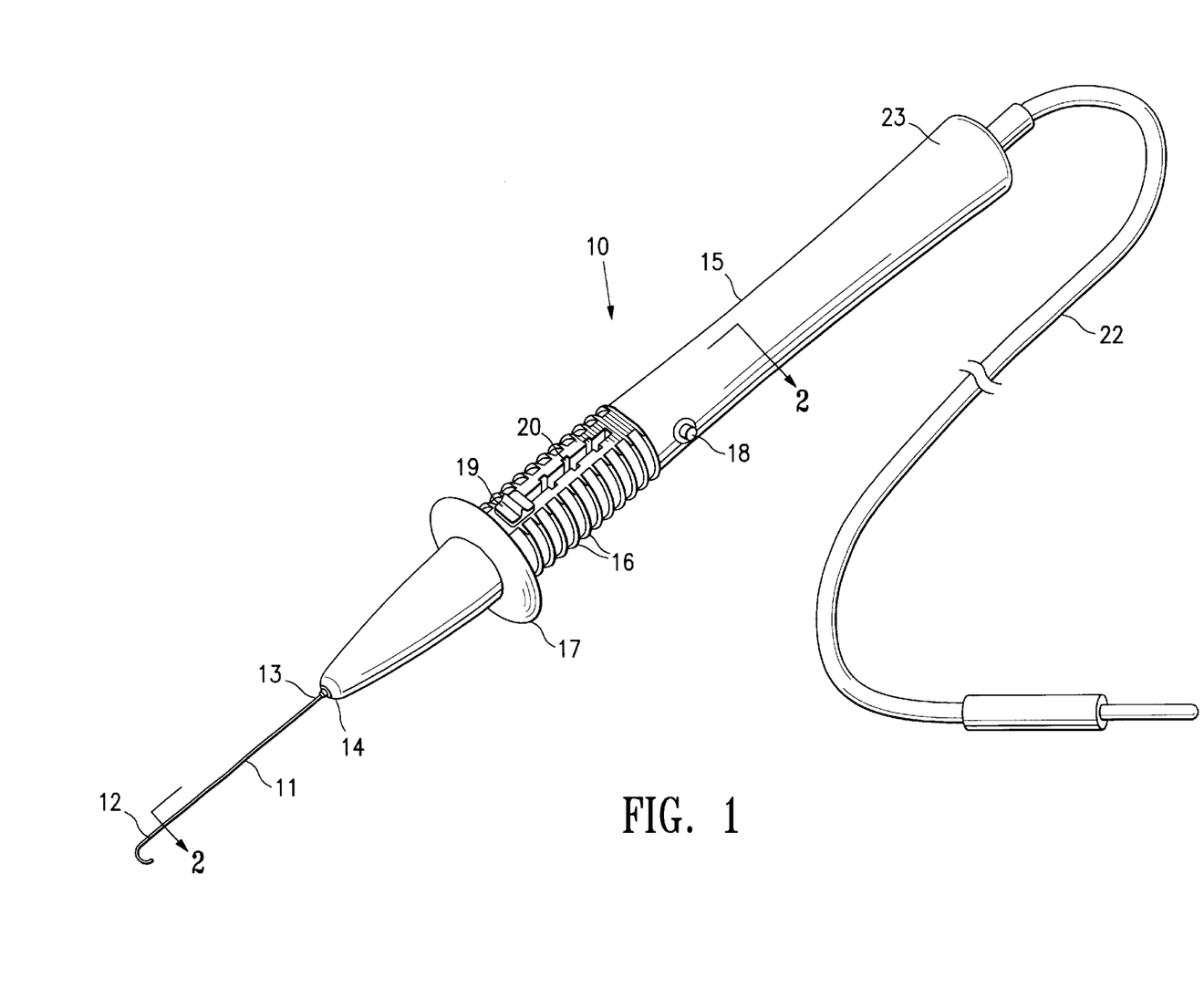
FIG. 1. is a perspective view of an electrosurgical cutting device which embodies features of the invention.
Figure 2:
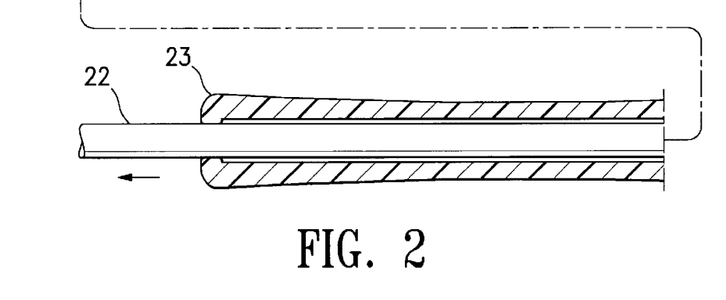
FIG. 2. is an elevational view, partially in section, of the electrosurgical device illustrated in FIG. 1.
Figure 3:
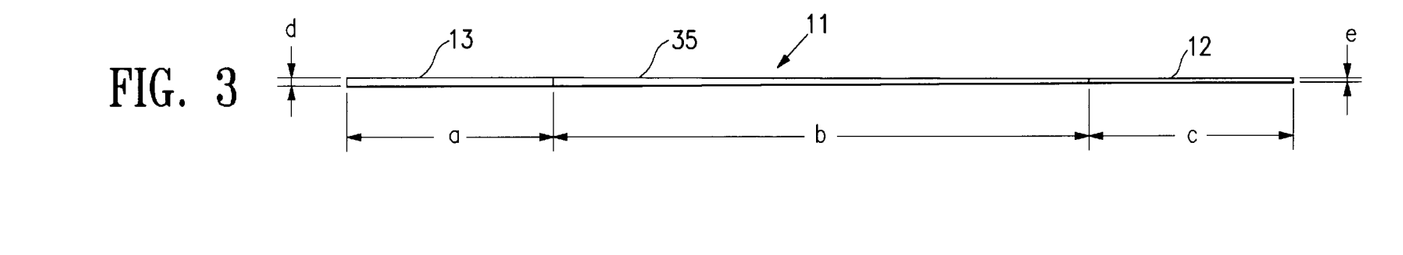
FIG. 3 is an elevational view of the electrosurgical electrode shown in the device of FIG. 2.
Figure 4:
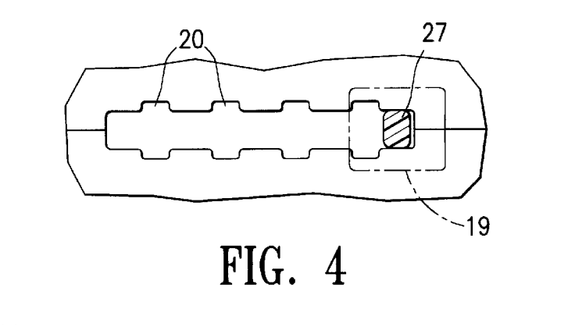
FIG. 4 is an enlarged plan view, partially in section, of the upper portion of the handle illustrated in FIG. 2 taken along the lines 4—4.
Figure 5:
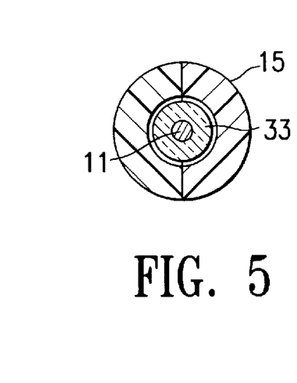
FIG. 5 is a transverse cross sectional view of the electrosurgical device illustrated in FIG. 2 taken along lines 5—5.

FIGS. 1–8 depict an electrosurgical cutting device 10 embodying various features of the invention which generally has a cutting electrode 11 with a free or exposed distal portion 12 and a proximal portion 13 which is secured within the distal end 14 of handle 15. The exterior of handle 15 is provided with ridges 16 configured for gripping by the physician or other operator to allow control of the device during operation and a radially extending flange 17 to protect the hand of the operator during operation of the electrosurgical device. The handle 15 is provided with a button type switch 18 for switching an RF electrode power source (not shown) to an active or "on" position or to an inactive or "off" position. A switching function may also be provided for alternative modes such as for coagulation. As best shown in FIGS. 2 and 4, the handle 15 may be provided with a thumb slide 19 to allow axial translation of an electrode assembly within the handle with detents 20 being provided to lock the thumb slide at various positions along a length of the handle. This allows the length of exposed electrode 11 which extends out the distal end 14 of the handle 15 to be adjusted to a desired length. A flexible cable 22 is provided for electrically coupling the cutting electrode 11 of the electrosurgical device 10 to an energizing source (not shown). The cable 22 enters the proximal end 23 of the handle 15 through an appropriate opening provided in the proximal end of the handle.

Figure 6:
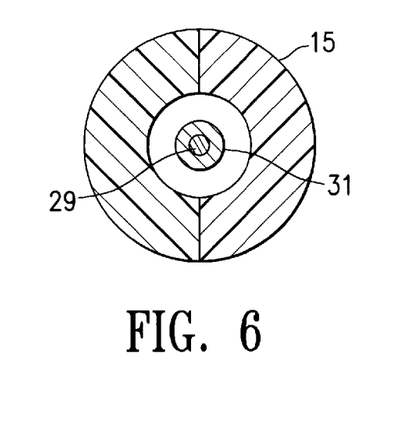
FIG. 6 is a transverse cross sectional view of the electrosurgical device of FIG. 2 taken along lines 6—6.
Figure 7:
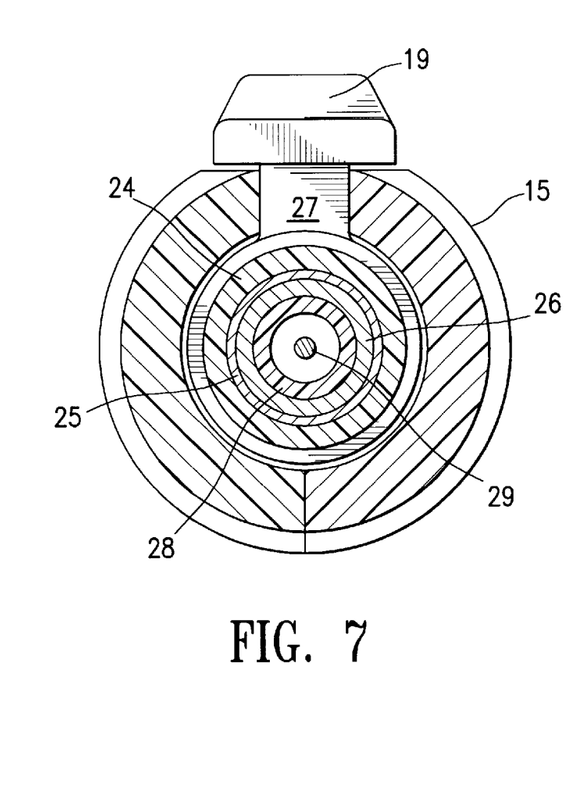
FIG. 7 is a transverse cross sectional view of the electrosurgical device illustrated in FIG. 2 taken along the lines 7—7.
Figure 8:
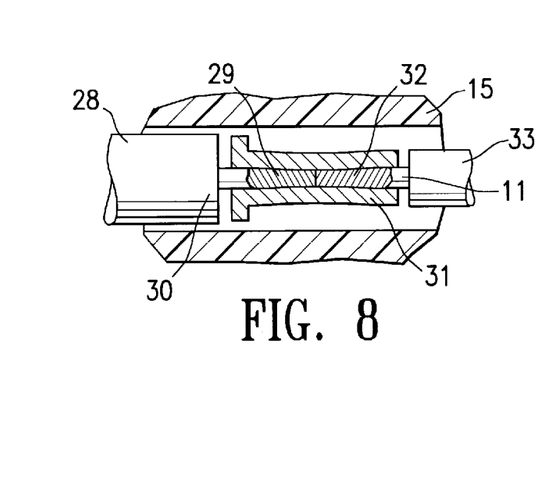
FIG. 8. is a longitudinal cross-sectional view taken of the area 8 shown in FIG. 2.

Details of the interior of the handle 15 are illustrated in FIGS. 2 and 5–8. The cable 22 extends through the interior of handle 15. The outer layer 24 and the shielding layer 25 of the cable 22 are secured to the ring or proximal eyelet 26 connected to the thumb slide 19 through lever 27 as shown in FIG. 7. The inner layer 28 and the inner electrical conductor 29 extend through an inner lumen (not shown) in the proximal eyelet 26 into the distal portion of the handle 15. As shown in more detail in FIGS. 6 and 8, the inner electrical conductor 29 extends beyond the distal end 30 of the inner layer 28 into the proximal end of metallic connector 31. The proximal end 32 of the cutting electrode 11 extends into the distal end of the metallic connector 31 which brings the cutting electrode 11 into an end to end electrically conducting relationship with the inner electrical conductor 29 of cable 22 as shown or in an overlapping or other configuration if desired. The metallic connector 31 is crimped onto the ends of the conductor 29 and the electrode 11 and is preferably formed of conducting material such a brass to facilitate passage of the high frequency electrical current from the inner conductor 29 to the proximal end of the cutting electrode 11.

Figures 9, 10:
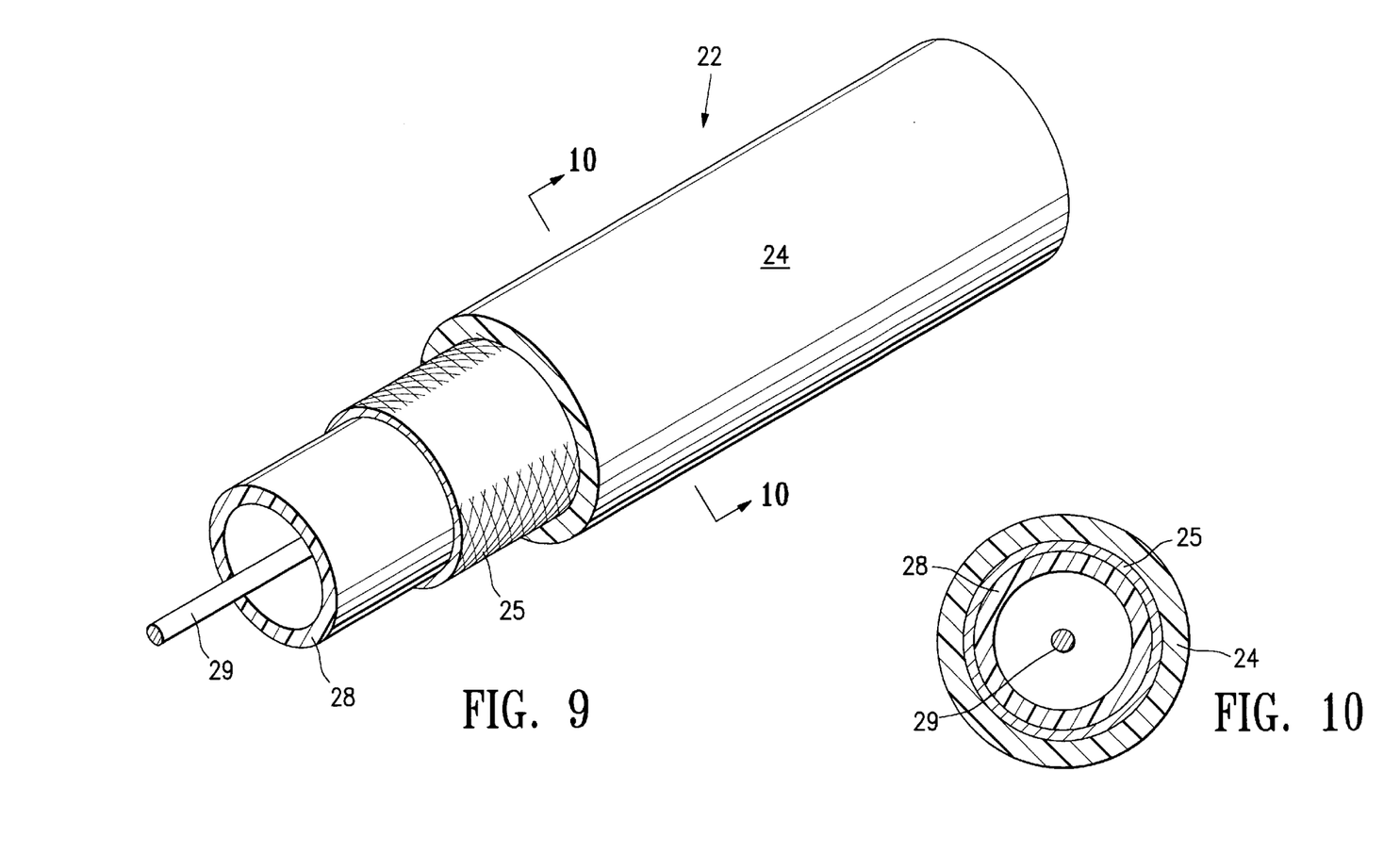
FIG. 9 is a cut away perspective view of a flexible shielded cable embodying features of the invention.
FIG. 10 is a transverse cross sectional view of the shielded cable illustrated in FIG. 9 taken along lines 10—10.

The flexible cable 22 is shown in more detain in FIGS. 9 and 10. The inner conductor 29 of cable 22 is typically made of solid copper wire about 0.0126 to about 0.037 inch (0.32–0.94 mm) in diameter, preferably about 0.0159 to about 0.021 inch (0.4–0.53 mm). Typically 26 AWG copper wire is utilized. The inner conductor 29 may be plated with silver or gold to provide more surface conductivity to accommodate the skin effect of RF currents when such currents propagate in a conductor. Alternatively, a layer of flexible polymeric material such as a cross linked modified polyester, an amide-imide copolymer or a polyurethane may circumferentially coat a solid inner conductor 29. A stranded inner conductor may be covered with a thin wall insulation material that is not affected by the sterilization method. The inner surface of the inner layer 28 defines an air gap or space between the inner layer and the inner conductor 29. The inner conductor 29 is unsupported or minimally supported along the length of the cable 22 which allows the inner conductor 29 to move more freely or "float" within the cable 22 to provide greater flexibility to the cable and lower power losses through reduced cable capacitance. Typically, the air gap diameter is about 0.08 to about 0.14 inch (2–3.6 mm), preferably about 0.1 to about 0.11 inch (2.5–2.8 mm). The inner and outer polymeric layers are conventional silicone or polyethylene layers about 0.03 to about 0.045 inch (0.76–1.14 mm) in thickness. The shielding layer 25 is preferably a multistranded braid or spiral wrap of conductive material such as copper. The strands of the braid or wrap may be about 0.15 to about 0.230 inch (3.8–5.8 mm) in diameter. The construction of the cable 22 is controlled to provide a radius of curvature of about 2 to about 5 inches (5–12.7 cm), preferably about 3 to about 4 inches (7.6–10.2 mm) without kinking. In an alternate embodiment the cable shielding layer 25 may be formed of an electrically conductive foil. The shielding layer 25 is typically grounded to reduces exposure of the operator of the electrosurgical device, as well as the patient and others, to RF radiation. The cable 22 is generally less than about 12 feet, preferably less than about 10 feet in length. Cables having lengths greater than 12 feet will usually have too high an impedance for effective tissue cutting through a variety of tissues, particularly fatty tissue.

As shown in FIG. 7 the outer layer 24 and shielding layer 25 are secured at the proximal end of proximal eyelet 26. The outer layer 24 circumferentially surrounds the shielding layer 25. The shielding braided layer 25 circumferentially surrounds the proximal eyelet and is typically joined to the proximal eyelet by soldering in which the solder is impregnated within the shielded layer. Alternatively, the shielding layer 25 may be joined to the proximal eyelet 26 by means of a crimp sleeve (not shown). The proximal eyelet 26 is generally made of brass but may alternatively be composed of other electrically conductive materials such as copper. The proximal eyelet 26 contains an aperture through which the inner layer 28 and inner conductor 29 pass through to the distal portions of the handle 15.

The proximal eyelet 26 is typically cylindrical and may be about 0.1 to about 0.5 inch (2.5–13 mm) in length and is generally made of brass although it may alternatively be made of other electrically conductive materials. In some embodiments with fixed exposed electrode lengths, the proximal eyelet 26 may be captured within the handle member cavity to secure an electrode assembly with respect to the handle 15.

Referring to FIGS. 2 and 6, an insulating ceramic hub 33 is disposed at the distal portion of the handle 15 and typically has a nosecone 34 which generally protrudes from the distal end 14 of the handle 15. The proximal portion 13 of the cutting electrode 11 extends through a passageway of ceramic hub 33 which is configured to allow slidable longitudinal movement of the proximal electrode portion 13 through the inner lumen to adjust the exposed length of electrode 11 which extends out the distal end of the handle 15. The ceramic hub 33 can be made of insulating material such as a mica glass material, e.g. Mycalex® which is available from Mykroy/Mycalex Ceramics of Clifton, N.J. Other insulating materials may also be utilized to form the hub 33. The ceramic hub 33 prevents heating and melting of the handle and allows for tracking of the electrosurgical device during the performance of tissue excision. In alternate embodiments with fixed exposed electrode lengths, the hub 33 may be molded about the proximal portion 13 of the electrode 11 into a fixed position with the electrode.

As shown in FIG. 3, the cutting electrode 11 may have a proximal portion 13 of uniform transverse dimensions, a distal portion 12 having uniform transverse dimensions smaller than those of the proximal portion and an intermediate portion 35 which tapers from the transverse dimensions of the proximal portion to the smaller transverse dimensions of the distal portion 12. The electrode 11 is made of tungsten and preferably an alloy of tungsten containing from 3 to about 25% (by wt) rhenium and typically about 5% rhenium. In alternate embodiments the electrode may be made of high temperature stainless steel or other suitable alloy compositions. The tapered intermediate portion 35 and the distal portion 12 of the electrode 11 will form most, if not all of the exposed length of the electrode 11 which may range from about 0.5 inch up to about 4 inches (1.3–10 cm), and may range typically from about 1 inch to about 2.5 inches (2.5–5.4 cm). The transverse dimensions of the tungsten or tungsten alloy electrode is preferably formed by centerless grinding tungsten wire to achieve the desired dimensions which is a conventional technique. The lengths of the tapered and the distal portions of the electrode 11 will be selected to provide a desired stiffness to the exposed of the electrode for the particular procedure to be performed. Typically, the distal portion is about 0.5 inch (1.3 cm), the intermediate tapered portion about 1.25 inch (3.2 cm) and the proximal portion about 0.5 inch (1.3 cm).

The handle member 15 is typically made of a dielectric material such as ABS plastic and is generally tubular in shape with rounded edges but it may be formed of other suitable polymeric materials. The connector eyelet 31 is typically made of brass but can be made of any suitable conductive material.

Figure 11:
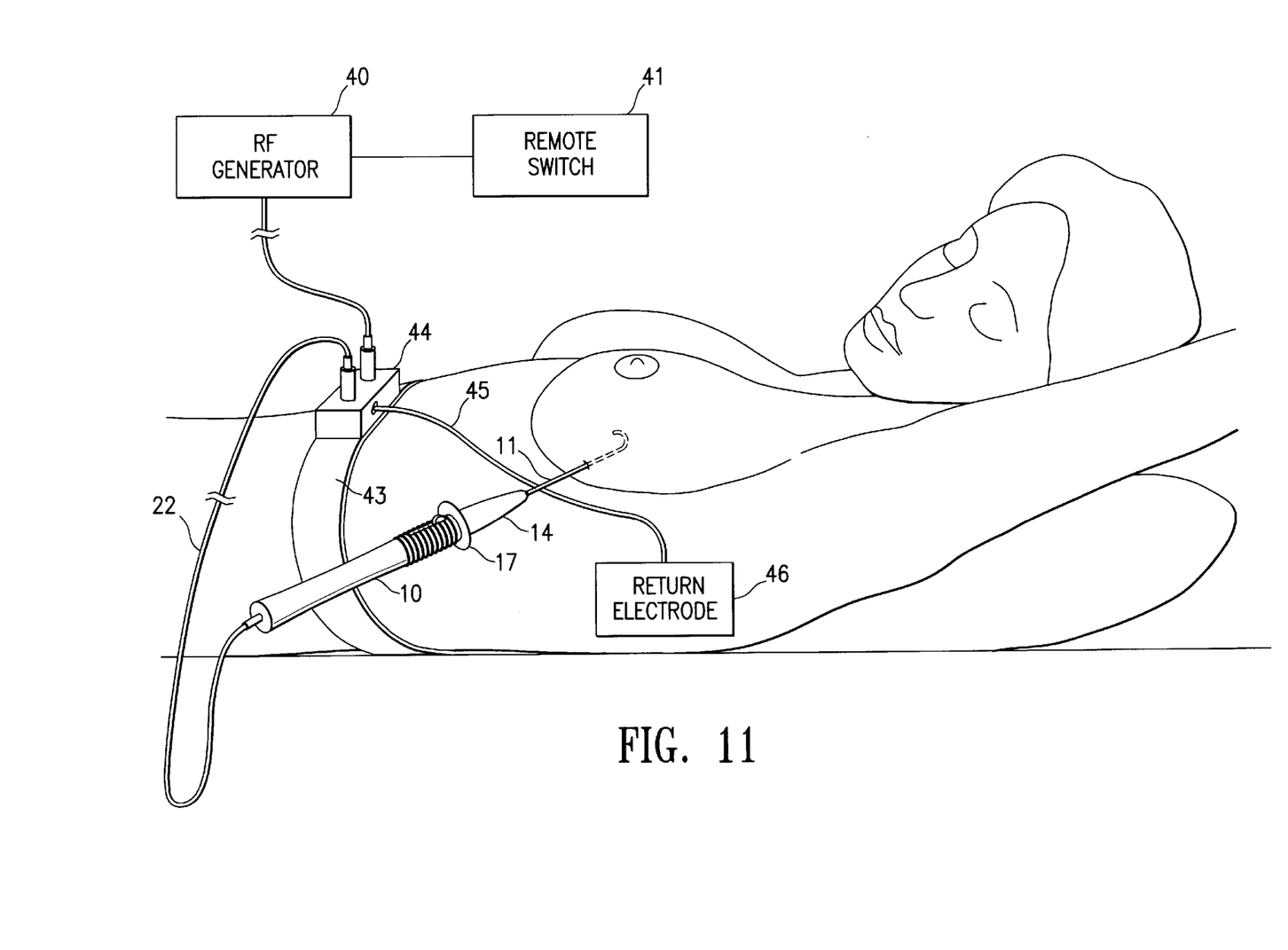
FIG. 11 is a schematic illustration of a female patient and an electrosurgical system embodying features of the invention for performing a breast biopsy.

FIG. 11. illustrates the electrosurgical system for the performance of breast biopsy. The electrosurgical device 10 having the features and embodiments discussed above is energized by a high frequency RF generator 40 by means of a remote switch 41. Typically, a transformer box 44 is connected to the patient by a waist strap 43. The electrosurgical device 10 is connected to the transformer box 44 which is connected to the radio frequency generator 40. An additional cable 45 connected to a transformer box 44 extends to an alternate or extra ground-electrode or pad 46 secured to the patient with an electrically conductive gel at the interface to complete the electrical circuit from the active electrode and thus prevent shock or injury to the patient. In alternate embodiments the ground electrode may be placed on other regions such as the patient's back, or abdominal region. In another embodiment a cable in electrical connection with the on/off button may extend from the external aspect of the handle to the transformer box which is in electrical connection to the RF generator thus allowing for the operational switching of the RF generator with the press of a button by the operator of the device. Alternate embodiments may involve controlling the energizing source with the use of a remote switch such as a foot pedal or a voice activated controller. Switching elements (not shown) may also be provided for other operating modes such as for coagulation. The details of the RF generator are set forth in concurrently filed application of the present assignee entitled High Frequency Power Source which is incorporated herein in its entirety.

Figure 12:
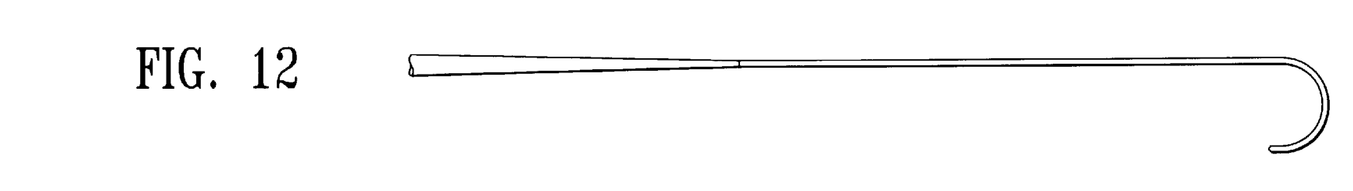
FIG. 12 is an illustration of a preformed cutting electrode having a "J" shape.
Figure 13:
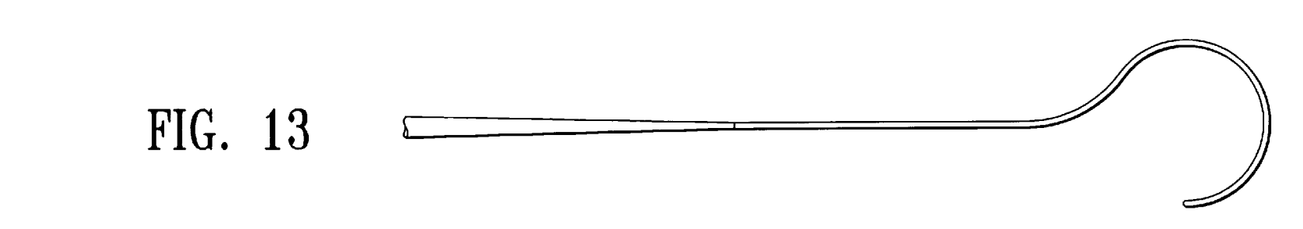
FIG. 13 is an illustration of a preformed cutting electrode having an alternative arcuate shape.
Figure 14:
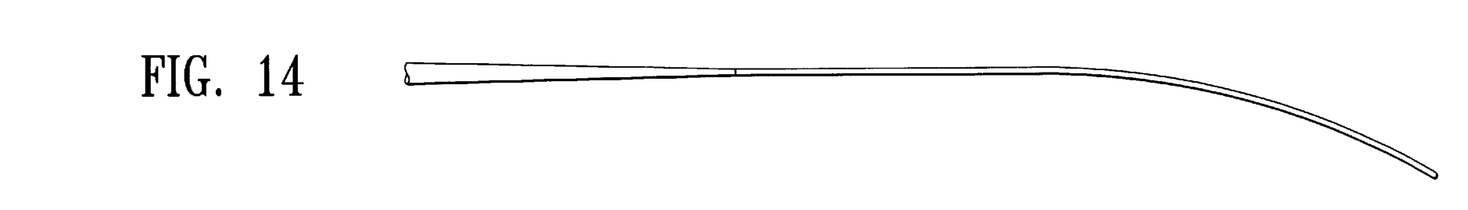
FIG. 14 is an illustration of a preformed cutting electrode having another alternative arcuate shape.

FIGS. 12, 13 and 14 illustrate examples of various shapes that can be provided for in the various embodiments of the invention having pre-shaped configurations of the electrode. FIG. 12 shows an electrosurgical preshaped electrode having a "J" shape configuration. FIGS. 13 and 14 show electrosurgical preshaped electrodes having alternative arcuate configurations In addition to the preshaped embodiments described above. Other useful shapes can be provided.

Figure 15:
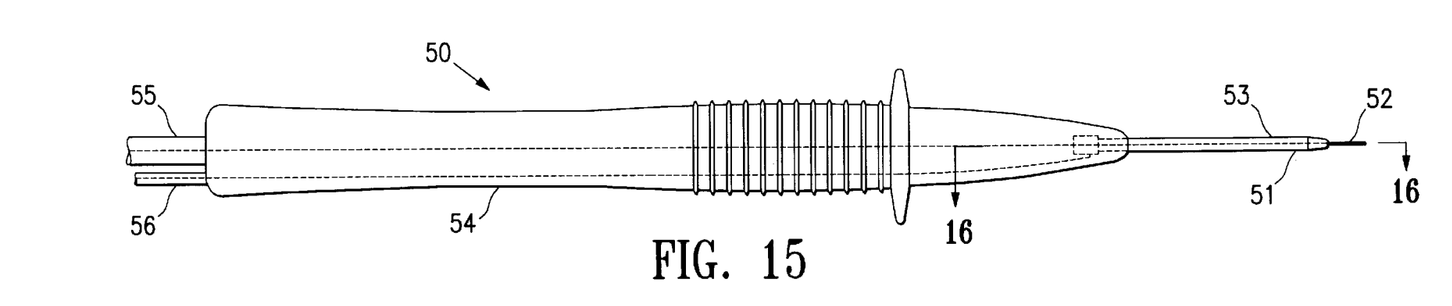
FIG. 15 is an elevational view of an alternative bipolar electrosurgical device embodying features of the present invention.
Figure 16:
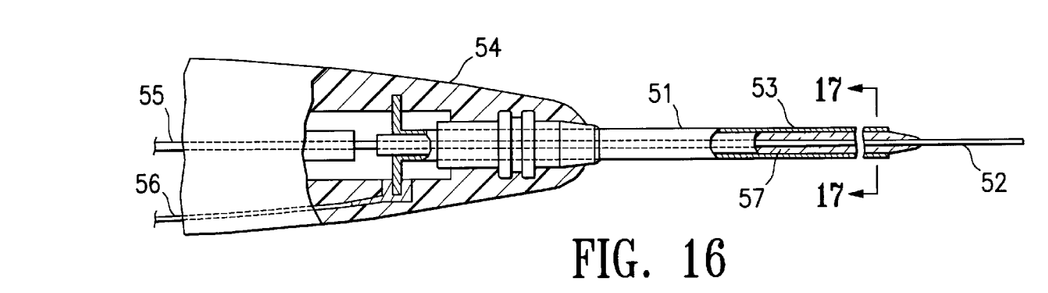
FIG. 16. is an enlarged elevational view, partially in section, of the distal end of the electrosurgical device illustrated in FIG. 15.
Figure 17:
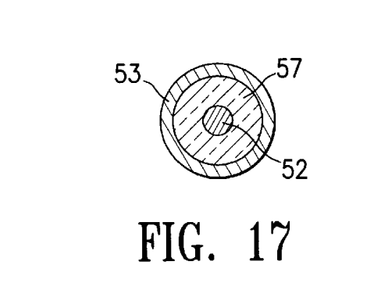
FIG. 17 is a transverse cross sectional view of the electrosurgical device shown in FIG. 16 taken along line 17—17.

FIGS. 15–17 illustrate a bipolar electrosurgical device embodying features of the invention. In this embodiment the electrosurgical instrument 50 has an electrode assembly 51 with a manually shapeable elongated primary electrode 52 surrounded circumferentially by a return electrode conductor 53. The proximal end of the electrode assembly 51 is secured to a handle 54 similar to handle 15 of the prior embodiment. The primary electrode 52 is electrically connected by a specialized cable/electrical conductor 55 (such as the cable 22 described above) which enters the proximal end of the handle 54 through an opening (not shown) in the proximal end of the handle and extends longitudinally to end in electrical connection with the primary electrode as indicated by the phantom lines. The return conductive electrode 53 is electrically connected by a separate cable 56 which enters the proximal portion of the handle member at the proximal end and travels longitudinally through the handle member cavity to end in electrical communication with the primary electrode as indicated by the phantom lines. The primary electrode is preferably formed of tungsten or alloys thereof as discussed above. The return conductive electrode 53 is generally a hollow cylindrical tube which circumferentially surrounds a portion of the proximal end of the primary electrode and is typically made of stainless steel but may alternatively be made of such material as tungsten or tungsten alloys as discussed above. An insulating material 57 is disposed between the primary and return electrodes 52 and 53 respectively The active electrode 52 generally extends beyond the distal end of the return electrode 53 and has an exposed length which is sufficient for the procedures to be conducted.

Figure 18:
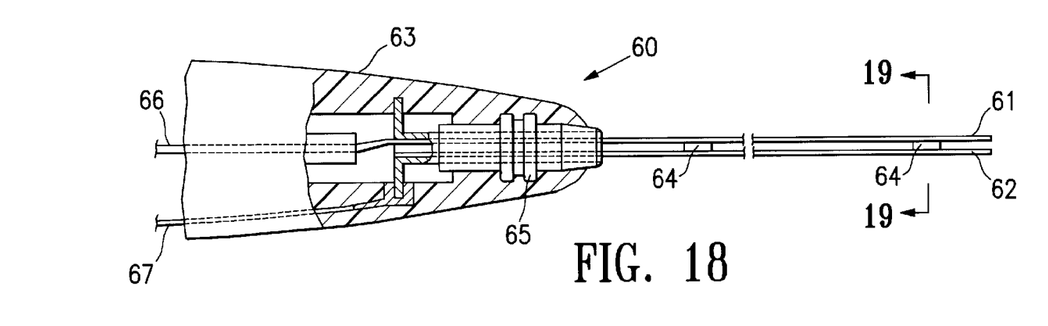
FIG. 18 is an enlarged cutaway view of the distal extremity of an alternative bipolar electrosurgical device similar to the device shown in FIGS. 15–17 but with parallel, side-by side electrodes.
Figure 19:
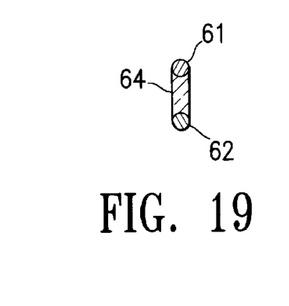
FIG. 19 is a transverse cross sectional view of the electrosurgical device illustrated in FIG. 18 taken along lines 19—19.

FIGS. 18 and 19 illustrate an alternative embodiment of a bipolar electrosurgical device 60 having a primary electrode 61 and a return electrode 62 with proximal and distal ends and a handle 63 similar to those previously described herein. Both the primary and return electrodes are preferably made of tungsten or alloys thereof but may be alternatively comprised of high temperature stainless steel or other compositions. The primary and return electrodes typically have an exposed length in the range such as 0.25 to about 2.5 inches (0.63–6.35 mm). The primary electrode 61 and the return electrode 62 extend generally parallel with respect to each other and are joined or stabilized in their parallel positions by one or more insulating ceramic stand-offs 64 which lie perpendicular between the longitudinal axis of the electrodes. The proximal ends of the primary and return electrodes 61 and 62 are attached to an insulating ceramic hub 65 which contains a lumen for receiving the proximal ends of the electrodes. The primary and the return electrodes 61 and 62 end in electrical communication with electrical conductors 66 and 67 respectively. The electrical conductors are configured for electrical connection to an RF generator (not shown).

The bipolar electrosurgical devices can be employed in a system such as that shown in FIG. 11 and the method of using the bipolar devices for performing a tissue excision is essentially the same as with a monopolar device as previously described.

The foregoing description details certain embodiments of the invention. Various modifications to the invention may be made without departing from its spirit or essential characteristics. The described embodiments are to be considered in all respects only as illustrative and not restrictive to the scope of the invention. Moreover, those skilled in the art will recognize that feature found in one embodiment may be utilized in another embodiment. Terms such as elements, members, devices and words of similar import when used herein shall not be construed as invoking the provisions of 35 U.S.C. §112(6) unless the following claims expressly use the term "means" or "step" followed by a particular function.

What is claimed is:

1. A hand-held electrosurgical cutting device comprising:
a handle which has a proximal end, a distal end and an inner lumen; and
an elongated manually shapeable cutting electrode, which is formed at least in part of a conductive metallic material, which has a proximal portion slidably secured within the inner lumen of the handle, which has a distal portion having transverse cross sections less than the transverse cross section of the proximal portion and having a blunt free distal end, an intermediate tapered portion extending between the proximal and distal portions, which has an exposed active metallic surface extending over the distal portion and at least part of the tapered portion and having a length of at least about 0.25 inch and a maximum transverse dimension of not greater than about 0.03 inch.

2. The electrosurgical device of claim 1 wherein the cutting electrode has an exposed active surface over a length of about 0.75 inches to about 4 inches.

3. The electrosurgical device of claim 2 wherein the cutting electrode has an exposed active surface over a length of about 1.2 inches to about 2.5 inches.

4. The electrosurgical device of claim 1 wherein the cutting electrode has a transverse dimension over a substantial length thereof from about 0.007 to about 0.03 inch.

5. The electrosurgical device of claim 1 wherein the cutting electrode has a transverse dimension over a substantial length thereof from about 0.01 to about 0.02 inch.

6. The electrosurgical device of claim 1 wherein the intermediate portion of the cutting electrode tapers from a transverse dimension of at least 0.012 inch at the proximal portion of the electrode to a transverse dimension of less than about 0.012 inch in at the distal portion of the electrode.

7. The device of claim 1 wherein the intermediate portion of the cutting electrode tapers distally from a transverse dimension of between about 0.012 and about 0.018 inch at the proximal portion of the cutting electrode to a transverse dimension of between about 0.004 to about 0.01 inch at the distal portion of the cutting electrode.

8. The electrosurgical device of claim 1 wherein the cutting electrode is formed at least in part of a metallic material selected from the group consisting of tungsten, tungsten alloys, stainless steel, and combinations thereof.

9. The electrosurgical device of claim 8 wherein the metallic material is a tungsten alloy containing rhenium.

10. The electrosurgical device of claim 9 wherein the tungsten alloy contains from about 3% to about 25% rhenium.

11. The electrosurgical device of claim 1 wherein the metallic material is a stainless steel.

12. The electrosurgical device of claim 1 wherein the handle further comprises a slide configured to allow axial translation of at least part of the proximal portion of the elongated cutting electrode within the inner lumen of the handle.

13. The electrosurgical cutting device of claim 1 wherein the proximal portion of the cutting electrode is received and supported by a non-conductive hub at the distal end of the handle.

14. The device of claim 13 wherein the proximal portion of the elongated cutting electrode is secured to the hub.

15. The device of claim 13 wherein the hub is formed of mica glass.

16. A hand-held electrosurgical cutting device comprising:
a handle which has a proximal end and a distal end; and
a blunt-ended elongated manually shapeable cutting electrode which has a proximal portion, a tapered portion and a distal portion, which is slidably secured by its proximal portion within the handle, which is formed at least in part of a conductive metallic material, which has an active exposed section including the distal portion and at least part of the intermediate tapered portion configured for a sweeping cutting motion with a maximum transverse dimension of not greater than about 0.03 inch.

17. The electrosurgical device of claim 16 wherein the conductive metallic material is selected from the group consisting of tungsten and tungsten alloys.

18. The electrosurgical device of claim 17 wherein the conductive metallic material is a tungsten alloy which contains rhenium.

19. The electrosurgical device of claim 18 wherein the tungsten alloy contains from about 3% to about 25% rhenium.

20. The electrosurgical device of claim 17 wherein the cutting electrode has an exposed active section over a length of at least about 0.25 inch.

21. The electrosurgical device of claim 16 wherein the cutting electrode has an exposed active surface over a length of about 0.75 inches to about 4 inches.

22. The electrosurgical device of claim 16 wherein the cutting electrode has an exposed active surface over a length of about 1.2 inches to about 2.5 inches.

23. The electrosurgical device of claim 16 wherein the cutting electrode has a transverse dimension over a substantial length thereof of from about 0.007 to about 0.03 inch.

24. The electrosurgical device of claim 16 wherein the cutting electrode has a transverse dimension over a substantial length thereof of from about 0.01 to about 0.02 inch.

25. The electrosurgical device of claim 18 wherein the cutting electrode tapers from a transverse dimension above 0.012 inch at the proximal portion thereof to a transverse dimension of less than about 0.012 inch at the distal portion of the electrode.

26. The electrosurgical device of claims 18 wherein the intermediate portion of the cutting electrode tapers distally from a transverse dimension of between about 0.012 to about 0.018 inch at the proximal portion of the cutting electrode to a transverse dimension of between about 0.004 to about 0.01 inch at the distal portion of the cutting electrode.

27. A hand-held electrosurgical cutting device comprising:
a) a handle which has a proximal end and a distal end;
b) an elongated manually shapeable cutting electrode which has a proximal portion secured to the handle, an intermediate tapered portion having a maximum transverse dimension of not greater than about 0.03 inch and a distal portion with a blunt free end and which has an exposed active metallic surface extending over the distal portion and at least part of the intermediate portion; and c) a flexible coaxial cable which is secured to the proximal end of the handle, which is electrically connected to the cutting electrode, which has an inner electrical conductor extending the length thereof unsupported within a jacket and which has a gas filled interior between the jacket and the electrical conductor.

28. The electrosurgical cutting device of claim 27 wherein the inner electrical conductor of the cable is made of conductive wire having a diameter of between about 0.013 to about 0.04 inch (0.32–0.94 mm).

29. The electrosurgical cutting device of claim 27 wherein the inner electrical conductor of the cable is made of a conductive wire having a diameter of between about 0.016 to about 0.02 inch (0.4–0.53 mm).

30. The electrosurgical cutting device of claim 27 wherein the distal portion of the cutting electrode has an exposed active section with a length of at least about 0.25 inch.

31. The electrosurgical device of claim 27 wherein the cutting electrode has an exposed active surface over a length of about 0.75 inches to about 4 inches.

32. The electrosurgical device of claim 27 wherein the cutting electrode has an exposed active surface over a length of about 1.2 inches to about 2.5 inches.

33. The electrosurgical device of claim 27 wherein the cutting electrode has a transverse dimension over a substantial length thereof from about 0.007 to about 0.03 inch.

34. The electrosurgical device of claim 27 wherein the cutting electrode has a transverse dimension over a substantial length thereof from about 0.01 to about 0.02 inch.

35. The electrosurgical device of claim 30 wherein the cutting electrode tapers from a transverse dimension above 0.012 inch in a proximal portion thereof to a transverse dimension of less than about 0.012 inch in a distal portion of the electrode.

36. The electrosurgical device of claim 30 wherein the cutting electrode tapers distally from a transverse dimension of between about 0.012 to about 0.018 inch at the proximal portion of the cutting electrode to a transverse dimension of between about 0.004 to about 0.01 inch at the distal portion of the cutting electrode.

37. The electrosurgical device of claim 27 wherein the cutting electrode comprises a metallic material.

38. The electrosurgical device of claim 37 wherein the cutting electrode comprises a metallic material selected from the group consisting of tungsten, steel and alloys and combinations thereof.

39. The electrosurgical device of claim 27 wherein the cutting electrode comprises a tungsten alloy containing rhenium.

40. The electrosurgical device of claim 39 wherein the tungsten alloy contains from about 3% to about 25% rhenium.

41. The electrosurgical device of claim 37 wherein the metallic material comprises a stainless steel.

42. The electrosurgical device of claim 27 wherein the handle is provided with an inner lumen and the proximal portion of the cutting electrode is slidably disposed within said inner lumen of the handle.

43. The electrosurgical device of claim 27 wherein the handle further comprises a slide configured to allow axial translation within the inner lumen of the handle.

44. The electrosurgical cutting device of claim 27 wherein the proximal portion of the cutting electrode is received and supported by a non-conductive hub at the distal end of the handle.

45. The device of claim 44 wherein the proximal portion of the cutting electrode is secured to the hub.

46. A hand-held electrosurgical system comprising:
a) an electrosurgical cutting device comprising:
a handle which has a proximal end and a distal end; and
an elongated manually shapeable cutting electrode which has a proximal portion secured to the handle, which has an intermediate, distally tapering portion with a maximum transverse dimension of not greater than 0.03 inch, which has a distal portion with a blunt free distal end and which has an active exposed metallic extending over the distal portion and at least part of the Intermediate portion of the electrode; and
b) a radiofrequency (RF) electrical power generator which has a frequency output of between about 1 to about 10 megahertz and which is electrically connected to the cutting electrode.

47. The electrosurgical system of claim 46 including at least one ground electrode configured to complete an electrical circuit between the cutting electrode and the RF generator.

48. The electrosurgical system of claim 46 including at least one transformer box configured to complete an electrical circuit between the RF generator and the cutting electrode.

49. The electrosurgical system of claim 46 wherein the RF generator is configured to produce an electrical output having an essentially sinusoidal waveform.

50. The electrosurgical system of claim 49 wherein the sinusoidal waveform has a total harmonic distortion less than about 5%.

51. The system as defined in claims 47, wherein the power output of the RF generator has a frequency of between about 3 MHz to about 8 MHz.

52. The system as defined in claim 46 wherein the cutting electrode is part of a bipolar electrode assembly.

53. A method of cutting tissue, comprising:
a) providing an electrosurgical device which has an elongated manually shapeable cutting electrode with a tapered portion and a blunt free distal end and with an active section extending over a length of at least about 0.25 inch and having a maximum transverse dimension of not greater than about 0.03 inch;
b) placing at least part of the active section of the cutting electrode in contact with tissue to be cut;
c) providing electrical power to the cutting electrode at a frequency of at least one megahertz; and
d) advancing the cutting electrode through tissue while said electrical power is provided to the elongated cutting electrode.

54. The method of claim 53 further comprising manually shaping the cutting electrode to a preferred configuration prior to contacting the tissue.

55. The method of claim 53 wherein the electrical power provided to the cutting electrode has an essentially sinusoidal waveform.

56. A hand-held bipolar electrosurgical cutting device comprising:
a) a handle having proximal and distal ends; and
b) an elongated bipolar electrode assembly which has a proximal portion, a distally tapering intermediate portion and a distal portion, which is slidably secured by its proximal portion to the distal end of the handle, which has an elongated manually shapeable primary cutting electrode with a blunt free end having an active exposed section with a maximum transverse dimension of not greater than about 0.03 inch and a length of at least about 0.25 inch and which has a return electrode comprising a sleeve electrode disposed about the primary electrode proximal to the active exposed section.

57. The bipolar electrode assembly of claim 56 including a high frequency electrical power generator having an electrical output at a frequency of between about 1 and about 10 megahertz.

58. The bipolar electrode assembly of claim 57 including a first cable connecting the proximal end of the primary electrode with the high frequency electrical power generator.

59. The bipolar electrode assembly of claim 58 including a second cable connecting the proximal end of the sleeve electrode with the high frequency electrosurgery generator.

60. The bipolar electrosurgical cutting device of claim 58 wherein the exposed length of the primary electrode extends beyond the return sleeve.

61. A method of cutting heterogeneous tissue including fatty tissue comprising:
    a) providing an elongated cutting electrode which has a proximal portion, a distally tapering intermediate portion and a distal portion with a blunt free distal end and which has an exposed section with a length of at least 0.25 inch and a maximum transverse dimension of not greater than 0.03 inch;
    b) passing electrical current to the cutting electrode having a frequency of between about 1 to about 10 megahertz;
    c) applying at least part of the cutting electrode to tissue; and
    d) controlling the electrical current passed to the cutting electrode based upon a voltage setpoint.

62. The method of claim 64 wherein the electrical current passed to the cutting electrode is controlled based upon a first voltage setpoint at the initiation of the cutting tissue and on a second voltage setpoint after the initiation of the cutting tissue.

63. The method of claim 62 wherein the first voltage setpoint is between about 450 Vrms to about 550 Vrms.

64. The method of claim 63 wherein the second voltage setpoint is between about 550 Vrms to about 650 Vrms.

65. A hand-held electrosurgical cutting device comprising:
    a handle which has a proximal end, a distal end, and an inner lumen; and
    an elongated manually shapeable cutting electrode, which is formed at least In part of a conductive metallic material, which has a proximal portion slidably secured within said inner lumen of the handle, which has a distally tapering intermediate portion and a distal portion with a blunt free distal end and which has an exposed active section over a length of at least about 0.25 inch with a maximum transverse dimension of not greater than about 0.03 inch.

66. A hand-held electrosurgical cutting device comprising:
    a handle which has a proximal end and a distal end; and
    an elongated manually shapeable cutting electrode which has a proximal portion, a distally tapering intermediate portion and a distal portion with a blunt free distal end, which has a maximum transverse dimension of not greater than about 0.03 inch over a length of at least 0.25 inch, which is secured by its proximal portion within the handle and which is formed at least in part of a conductive metallic material selected from the group consisting of tungsten, tungsten alloys, stainless steel, and combinations thereof.

67. A hand-held electrosurgical system comprising:
    a) an electrosurgical cutting device comprising, and
       a handle which has a proximal end and a distal end;
       an elongated manually shapeable cutting electrode which has a proximal portion slidably secured to the distal end of the handle, which has a distally tapering intermediate portion and which has a distal portion with a blunt free distal end and with a maximum transverse dimension of not greater than about 0.03 inch over a length of at least 0.25 inch; and
    b) a radiofrequency (RF) electrical power generator which is configured to have a frequency output of between about 1 to about 10 megahertz and which Is electrically connected to the proximal end of the elongated cutting electrode.

68. A hand-held bipolar electrosurgical cutting device comprising:
    a) a handle having proximal and distal ends; and
    b) an elongated manually shapeable bipolar electrode assembly which has proximal portion, a tapering intermediate portion and a distal portion, which is slidably secured by its proximal portion to the distal end of the handle, which has an elongated primary electrode with a blunt free distal end, an active exposed section having a length of at least about 0.25 inch and a maximum transverse dimension of not greater than about 0.03 inch over the length, and which has a return electrode with a sleeve electrode disposed about the primary electrode.

69. A hand-held electrosurgical cutting device comprising:
    a. a handle which has a proximal end and a distal end; and
    b. an elongated manually shapeable cutting electrode which has a proximal portion, a tapering intermediate portion having a maximum transverse dimension of not greater than 0.03 inch and a distal portion, which is secured by its proximal portion to the handle, which is formed at least in part of a conductive metallic material and which has an active exposed surface having a length of at least 0.5 inch, at least part of which extends over the intermediate portion.

70. The electrosurgical device of claim 69,wherein the length of the tapered portion of the cutting electrode is about 0.5 inch to about 4 inches.

71. The electrosurgical device of claim 69 wherein the length of the tapered portion of cutting electrode is about 1 inch to about 2.5 inches.

72. The electrosurgical device of claim 69 wherein the tapered portion of the cutting electrode has a maximum transverse dimension of about 0.01 to about 0.02 inch.

73. The electrosurgical device of claim 69 wherein the tapered portion of the cutting electrode has a minimum transverse dimension of about 0.004 to about 0.01 inch.

* * * * *